(12) United States Patent
Yu et al.

(10) Patent No.: US 6,878,374 B2
(45) Date of Patent: Apr. 12, 2005

(54) BIODEGRADABLE POLYACETALS

(75) Inventors: Lei Yu, Carlsbad, CA (US); Sang Van, San Diego, CA (US); Shouping Ji, Oceanside, CA (US); Kenji Matsumoto, San Diego, CA (US)

(73) Assignee: Nitto Denko Corporation (JP)

( * ) Notice: Subject to any disclaimer, the term of this patent is extended or adjusted under 35 U.S.C. 154(b) by 137 days.

(21) Appl. No.: 10/375,705

(22) Filed: Feb. 25, 2003

(65) Prior Publication Data

US 2004/0166089 A1 Aug. 26, 2004

(51) Int. Cl.$^7$ .................... A61K 39/44; C08F 283/00
(52) U.S. Cl. .................... 424/178.1; 528/332; 528/363; 528/364; 528/376; 528/392; 528/422; 528/425; 525/535; 525/540; 514/579; 514/609; 514/613; 514/716; 514/722; 514/723; 424/178.1; 424/1.53; 424/179.1; 530/391.5; 530/402
(58) Field of Search .................... 528/332, 363, 528/364, 376, 392, 422, 425; 525/535, 540; 514/579, 609, 613, 716, 722, 723; 424/178.1, 1.53, 179.1; 530/391.5, 402

(56) References Cited

U.S. PATENT DOCUMENTS

| 5,958,398 A | 9/1999 | Papisov |  |
|---|---|---|---|
| 6,331,311 B1 | 12/2001 | Brodbeck et al. | ............ 424/425 |
| 2002/0034532 A1 | 3/2002 | Brodbeck et al. | ............ 424/422 |

FOREIGN PATENT DOCUMENTS

| EP | 0 949 905 B1 | 7/2001 |
|---|---|---|
| WO | WO 92/11844 | 7/1992 |
| WO | WO 98/27962 | 7/1998 |
| WO | WO 98/27963 | 7/1998 |
| WO | WO 02/15955 A2 | 2/2002 |
| WO | WO 02/20663 A2 | 3/2002 |
| WO | WO 02/49573 A2 | 6/2002 |

OTHER PUBLICATIONS

Basko, M. et al., "Synthesis of Double Hydrophilic Graft Copolymers with a Polyacetal Backbone," Macromolucules, 2002, 35, pp. 8948–8953.

(Continued)

Primary Examiner—Samuel A. Acquah
(74) Attorney, Agent, or Firm—Knobbe Martens Olson & Bear LLP

(57) ABSTRACT

A polymer comprising recurring units represented by formula (I):

wherein X is selected from the group consisting of $C(O)OR^1$, $C(O)SR^1$, $C(O)NR^1R^2$, and VZ, where $R^1$ and $R^2$ are each individually selected from the group consisting of hydrogen, $C_1$ to $C_{10}$ alkyl, and $C_6$ to $C_{10}$ aryl, where V is a labile linker group, and where Z is selected from the group consisting of poly (ethyleneimine), poly(propyleneimine), poly(lysine), PAMAM dendrimer, octaamine dendrimer, and hexadecaamine dendrimer; and wherein Y is selected from the group consisting of $-(CH_2)_2-$, $-(CH_2)_2-O-(CH_2)_2-$, $-(CH_2)_2-O-(CH_2)_2-$, and $-(CH_2)_3-NHC(O)-(CH_2)_6-C(O)NH-(CH_2)_3-$ is useful in nucleic acid delivery applications. Polyacetals of the formula (I) are preferably made by reacting appropriate diols and divinyl ethers. In preferred embodiments, complexes formed between polyacetals of the formula (I) and polynucleotides are useful as transfection reagents.

20 Claims, 8 Drawing Sheets

OTHER PUBLICATIONS

Carpino, L.A. et al.; "The 9–Fluorenylmethoxycarbonyl Amino–Protecting Group," J. Org. Chem., 1972, 37, pp. 3404–3409.

Godbey, W.T. et al.; "Size matters: Molecular weight affects the efficiency of poly(ethylenimine) as a gene delivery vehicle," J. Biom. Mat. Res. Part A., 1999, 45, pp. 268–275.

Torres, L.F. et al.; "A New Polymerization System for Bicyclic Acetals: Toward the Controlled/" Living" Cationic Ring–Opening Polymerization of 6.8–Dioxabicyclo[3.2.1] octane," Macromolecules, 1999, 32, pp. 6958–6962.

Ahn, Cheol–Hee et al., "Biodegradable poly(ethylenimine) for plasmid DNA delivery," Journal of Controlled Release 80 (2002), pp. 273–282.

Brazeau, Gayle A., "In Vitro Myotoxicity of Selected Cationic Macromolecules Used in Non–Viral Gene Delivery," Pharmaceutical Research, vol. 15, No. 5, 1998, pp. 680–684.

Choksakulnimitr, Suthummar et al., "In vitro cytotoxicity of macromolecules in different cell culture systems," Journal of Controlled Release 34 (1995) pp. 233–241.

Lim, Yong–Beom et al., "Biodegradable Polyester, Poly [α–(4–Aminobutyl)–L–Glycolic Acid], as a Non–Toxic Gene Carrier," Pharmaceutical Research, vol. 17, No. 7, 2000, pp. 811–816.

Lim, Yong–Beom et al., "Biodegradable, Endosome Disruptive, and Cationic Network–type Polymer as a Highly Efficient and Nontoxic Gene Delivery Carrier," Bioconjugate Chem. 2002, 13, pp. 952–957.

Lim, Yong–Beom et al., "Cationic Hyperbranched Poly(amino ester): A Novel Class of DNA Condensing Molecule with Cationic Surface, Biodegradable Three–Dimensional Structure, and Teriary Amine Groups in the Interior," Journal of American Chemical Society 2001, 123, pp. 2460–2461.

Luo, Dan et al., "Synthetic DNA delivery systems," Nature Biotechnology, vol. 18, Jan. 2000, pp. 33–37.

Lynn, David M. et al., "Accelerated Discovery of Synthetic Transfection Vectors: Parallel Synthesis and Screening of a Degradable Polymer Library," Journal American Chemical Society 2001, 123, pp. 8155–8156.

Mulligan, Richard C., "The Basic Science of Gene Therapy," Science, vol. 260, May 14, 1993, pp. 926–932.

Murthy, Niren et al., "A Novel Strategy for Encapsulation and Release of Proteins: Hydrogels and Microgels with Acid–Labile Acetal Cross–Linkers," Journal American Chemical Society 2002, 124, pp. 12398–12399.

Tomlinson, Ryan et al., "Pendent Chain Functionalized Polyacetals That Display pH–Dependent Degradation: A Platform for the Development of Novel Polymer Therapeutics," Macromolecules 2002, 35, pp. 473–480.

Tuominen, Jukka et al., "Biodegradation of Lactic Acid Based Polymers under Controlled Composting Conditions and Evaluation of the Ecotoxicological Impact," Biomacromolecules 2002, 3, pp. 445–455.

Tomlinson, Ryan et al., "Polyacetal–Doxorubicin Conjugates Designed for pH–Dependent Degradation," Bioconjugate Chem. 2003, 14, pp. 1096–1106.

International Search Report for International Application No. PCT/US2004/005363 dated Jul. 12, 2004.

Transfection of 293 cells with pCMV-luc using polyacetal 10 and Lipofectamine (L2000, positive control). Labeling: ratio of polymer:DNA (weight:weight) for vertical line bar is 16:1, horizontal line bar is 8:1, downward line bar is 4:1, and grid line bar is 2:1.

GFP signals in cells 293 using polyacetal 10 and poly (ethylenimine-1800).
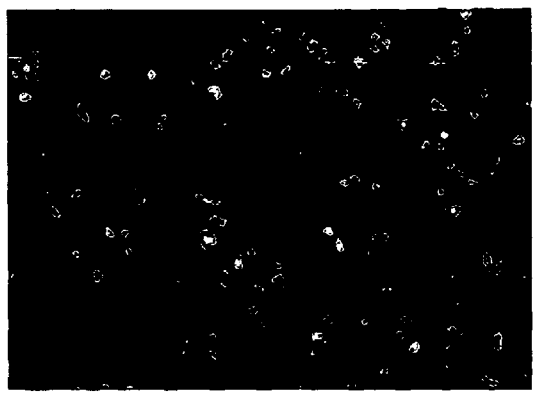
GFP signals using polyacetal 10         Control: GFP signals using PEI 1800
*FIG. 3A*                    *FIG. 3B*

GFP signals resulting from acidic degradation of polyacetal 10 in pH 5.0 and pH 6.0 buffers after 24 hours and 48 hours.

GFP signals 10 at pH 5.0 after 24h

GFP signals 10 at pH 5.0 after 48 h

GFP signals 10 at pH6.0 after 24 h

GFP signals 10 at pH 6.0 after 48 h

GGP signals for cells 293 using polyacetal 17 and poly (ethylenimine)-1800

GFP signals using polyacetal 17   Control: GFP signals using PEI-1800

Cytotoxicity of polyacetals 15, 12, and 10 and Lipofectamine (L2000). Labeling: ratio of polymer:DNA (weight:weight) for vertical line bar is 16:1, horizontal line bar is 8:1, downward line bar is 4:1, and grid line bar is 2:1.

BIODEGRADABLE POLYACETALS

BACKGROUND OF THE INVENTION

1. Field of the Invention

This invention relates generally to biodegradable polymers containing acetal recurring units. More particularly, this invention relates to acid sensitive biodegradable polyacetals, methods for making them, and methods for using them in polynucleotide delivery applications.

2. Description of the Related Art

There is a need for non-viral drug delivery systems having desirable properties such as low immunogenicity, amenable to production on a relatively large scale, and which can be easily modified to provide a range of biological properties. See Mulligan, R. C., "The basic science of gene therapy," Science 260, 926–932 (1993); and Luo, D. & Saltzman, W. M. "Synthetic DNA delivery systems," Nat. Biotechnol. 18, 33–37 (2000). However, non-degradable cationic polymers such as poly(lysine) and polyethyleneimine (PEI) can have significant cytotoxicity. See Choksakulnimitr, S., Masuda, S., Tokuda, H., Takakura, Y. & Hashida, M., "In vitro cytotoxicity of macromolecules in different cell culture systems," J. Control Release 34, 233–241 (1995); Brazeau, G. A., Attia, S., Poxon, S. & Hughes, J. A., "In Vitro Myotoxicity of Selected cationic macrolecules used in non-viral gene therapy," Pharm. Res. 15, 680–684 (1998); and Ahn, C.-H., Chae, S. Y., Bae, Y. H. & Kim, S. W. "Biodegradable poly(ethylenimine) for plasmid DNA delivery," J. Control. Release 80, 273–282 (2002).

To reduce cytotoxicity, some efforts have been made to develop degradable cationic polymers. See Ahn, C.-H., Chae, S. Y., Bae, Y. H. & Kim, S. W., "Biodegradable poly(ethylenimine) for plasmid DNA delivery," J. Control. Release 80, 273282 (2002); Lynn, D. M. A., D. G.; Putman, D; Langer, R., "Accelerated Discovery of Synthetic Transfection Vectors: Parallel Synthesis and Screening of a Degradable Polymer Library," J. Am. Chem. Soc. 123 (2001); Lim, Y. et al., "Biodegradable Polyester, Poly[α-(4-Aminobutyl)-1-Glycolic Acid], as a Non-toxic Gene Carrier," Pharmaceutical Research 17, 811–816 (2000); Lim, Y., Kim, S., Suh, H. & Park, J.-S., "Biodegradable, Endosome Disruptive, and Cationic Network-type Polymer as a High Efficient and Non-toxic Gene Delivery Carrier," Bioconjugate Chem. 13, 952–957 (2002); Lim, Y. K., S.; Lee, Y.; Lee, W.; Yang, T.; Lee, M.; Suh, H.; Park, J., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc. 123, 2460–2461 (2001); and Tuominen, J. et al., "Biodegradation of Lactic Acid Based Polymers under Controlled Composting Conditions and Evaluation of the Ecotoxicological Impact," Biomacromolecules 3, 445–455 (2002). However, under physiological conditions, these cationic polymers are susceptible to degradation via base-catalyzed hydrolysis.

Acid-sensitive polymers containing acetal linkages has been reported, see Tomlinson, R. et al., "Pendent Chain Functionalized Polyacetals That Display pH-Dependent Degradation: A Platform for the Development of Novel Polymer Therapeutics," Macromolecules 35, 473–480 (2002); and Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398–12399 (2002).

SUMMARY OF THE INVENTION

A preferred embodiment provides a polymer comprising recurring units represented by formula (I):

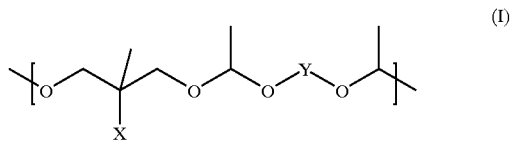

wherein X is selected from the group consisting of $C(O)OR^1$, $C(O)SR^1$, $C(O)NR^1R^2$, and VZ, where $R^1$ and $R^2$ are each individually selected from the group consisting of hydrogen, $C_1$ to $C_{10}$ alkyl, and $C_6$ to $C_{10}$ aryl, where V is a labile linker group, and where Z is selected from the group consisting of poly (ethyleneimine), poly(propyleneimine), poly(lysine), PAMAM dendrimer, octaamine dendrimer, and hexadecaamine dendrimer; and wherein Y is selected from the group consisting of $-(CH_2)_2-$, $-(CH_2)_2-O-(CH_2)_2-$, $-(CH_2)_2-O-(CH_2)_2-O-(CH_2)_2-$, and $-(CH_2)_3-NHC(O)-(CH_2)_6-C(O)NH-(CH_2)_3-$.

In another preferred embodiment, the polymer comprising recurring units represented by formula (I) further comprises a recurring unit represented by the formula (II):

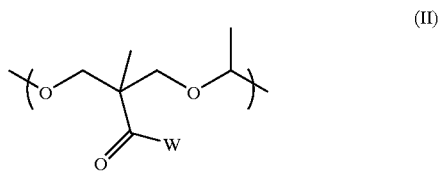

wherein W is selected from the group consisting of an enhancer and a targeting receptor.

Another preferred embodiment provides a method for making a polymer comprising recurring units represented by formula (I), comprising reacting a diol represented by the formula (III) with a divinyl ether represented by the formula (IV):

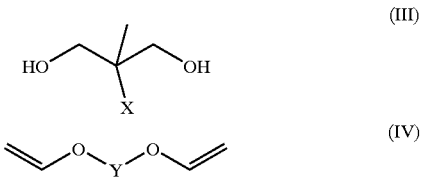

wherein X and Y have the same meanings as set forth above.

Another preferred embodiment provides a method for making a polymer comprising recurring units represented by formula (I) in which X is VZ, comprising reacting a compound represented by the formula $H_2NZ$ with a polymer comprising a recurring unit of the formula (V):

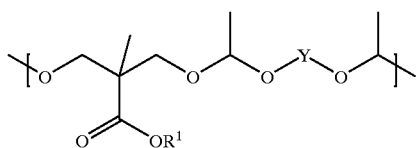

(V)

wherein Z is selected from the group consisting of poly (ethyleneimine), poly(propyleneimine), poly(lysine), PAMAM dendrimer, octaamine dendrimer, and hexadecaamine dendrimer; and wherein Y is selected from the group consisting of —$(CH_2)_2$—, —$(CH_2)_2$—O—$(CH_2)_2$—, —$(CH_2)_2$—O—$(CH_2)_2$—O—$(CH_2)_2$—, and —$(CH_2)_3$—NHC(O)—$(CH_2)_6$—C(O)NH—$(CH_2)_3$—.

Another preferred embodiment provides a complex, comprising (a) a polymer comprising recurring units represented by formula (I) in which X is VZ, and (b) a polynucleotide. Another preferred embodiment provides a method for making such a complex, comprising intermixing (a) a polymer comprising recurring units represented by formula (I) in which X is VZ, and (b) a polynucleotide.

Another preferred embodiment provides a method for transfecting a cell, comprising contacting the cell with a complex, wherein the complex comprises (a) a polymer comprising recurring units represented by formula (I) in which X is VZ, and (b) a polynucleotide.

These and other embodiments are described in greater detail below.

BRIEF DESCRIPTION OF THE DRAWINGS

FIG. 3 shows reproductions of photographs of Green Fluorescent Protein (GFP) signals using polyacetal 10 and a commercial cationic polymer, poly(ethylenimine)-1800 (molecular weight 1800 daltons, negative control). The results show that polyacetal 10 has a higher transfection efficiency than poly(ethylenimine)-1800.

DETAILED DESCRIPTION OF THE PREFERRED EMBODIMENTS

Figure 1:
FIG. 1 shows a reproduction of a photograph of a nucleotide retardation assay using polyacetal polymers and a DNA molecular marker. The assay shows that polyacetals 10 and 12 formed complexes with polynucleotides at various ratios of polyacetal to polynucleotide (16:1, 8:1, 4:1, and 2:1, weight/weight), as compared to a control C (no polyacetal) and a molecular marker M.

Preferred embodiments are directed to polyacetals, methods of making polyacetals, complexes comprising polyacetals and polynucleotides, methods of making such complexes, and methods of transfecting cells using such complexes.

Polyacetals are polymers that contain acetal (—O—CHR—O—) recurring units. Preferred polyacetals comprise recurring units represented by formula (I):

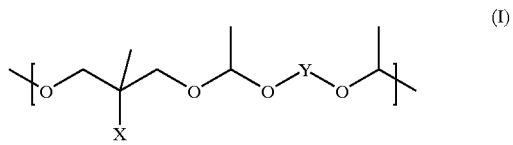

(I)

In formula (I), X is preferably selected from the group consisting of $C(O)OR^1$, $C(O)SR^1$, $C(O)NR^1R^2$, and VZ, where $R^1$ and $R^2$ are each individually selected from the group consisting of hydrogen, $C_1$ to $C_{10}$ alkyl, and $C_6$ to $C_{10}$ aryl, and where V is a linker group. In this context, "a linker group" is a bifunctional chemical group that joins one chemical group to another. Linker groups can contain a single bifunctional chemical group such as amide, or may contain two chemical groups such as amide-amide, amide-alkyl, alkyl-amide, amine-amide, or thioether-amide. Examples of preferred linker groups include —C(O)NH—, —C(O)NH—$R^1$—C(O)NH—, —C(O)NH—$R^1$—, —$R^1$—C(O)NH—, —NH—$R^1$—C(O)NH—, —S—$R^1$—C(O)NH, where $R^1$ is selected from the group consisting of hydrogen, $C_1$ to $C_{10}$ alkyl, and $C_6$ to $C_{10}$ aryl.

In formula (I), Z is preferably selected from the group consisting of poly(ethyleneimine) (PEI), poly(propyleneimine) (PPI), poly(lysine), polyamidoamine (PAMAM) dendrimers, octaamine dendrimers, and hexadecaamine dendrimers. PEI and PPI, if used, preferably have a molecular weight in the range of about 200 to about 100,000 Daltons. Poly(lysine), if used, preferably has a molecular weight in the range of about 200 to about 50,000 Daltons. In formula (I), Y is preferably selected from the group consisting of —$(CH_2)_2$—, —$(CH_2)_2$—O—$(CH_2)_2$—, —$(CH_2)_2$—O—$(CH_2)_2$—O—$(CH_2)_2$—O—$(CH_2)_2$—, and —$(CH_2)_3$—NHC(O)—$(CH_2)_6$—C(O)NH—$(CH_2)_3$—.

Polyacetals may be copolymers and thus may contain two or more different recurring units represented by the formula (I), and/or other recurring units. A "polyacetal of the formula (I)" or "polymer of the formula (I)", as those terms are used herein, includes such copolymers as well as homopolymers consisting essentially of recurring units of the formula (I). In a preferred embodiment, a polyacetal comprises a recurring unit of the formula (II):

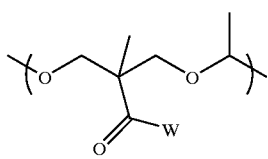

(II)

In formula (II), W is preferably selected from the group consisting of an enhancer and a targeting receptor. In this context, an "enhancer" is a functional group that is capable of enhancing the efficiency of gene transfection to a eukaryotic cell and a "targeting receptor" is a functional group that is capable of recognizing specific receptors on a cell surface. The foregoing definitions are not mutually exclusive, and thus W may be both an enhancer and a targeting receptor. Preferably, W is selected from the group consisting of lipid, cholesterol, transferrin, antibody, antibody fragment, galactose, mannose, lipoprotein, lysosomotrophic agent, and fusogenic agent. A "polyacetal of the formula (II)" or "polymer of the formula (II)", as those terms are used herein, includes copolymers comprising a recurring unit of the formula (II) as well as homopolymers consisting essentially of recurring units of the formula (II). A preferred polyacetal comprises a recurring unit of the formula (I) and a recurring unit of the formula (II).

Enhancers and/or a targeting receptors may be attached to polyacetals in various ways, e.g., by covalent bonding to the polyacetal as shown in formula (II), by conjugating an enhancer and/or a targeting receptor to Z in formula (I), or both. For example, in a preferred embodiment, a polyacetal comprises a recurring unit of the formula (I) and a recurring unit of the formula (II) in which X in formula (I) is VZ. The Z group in formula (II) may be conjugated to W (in which case the enhancer and/or a targeting receptor represented by W is attached to the polyacetal in at least two places, via conjugation to Z and covalent attachment to the recurring unit represented by the formula II), and/or the Z group in formula (II) may be conjugated to a second enhancer and/or second targeting receptor. Thus, two or more enhancers and/or a targeting receptors may be attached to a polyacetal.

Various methods may be used to make polyacetals. A preferred method comprises reacting a diol represented by the formula (III) with a divinyl ether represented by the formula (IV):

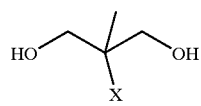

(III)

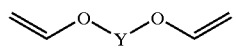

(IV)

In formulae (III) and (IV), X and Y have the same meanings as set forth above. The polymerization reaction is preferably conducted by intermixing a diol represented by the formula (III) with a divinyl ether represented by the formula (IV) in a polar aprotic solvent such as tetrahydrofuran in the presence of an acid catalyst such as p-toluenesulfonic acid (pTSA). Optionally, the mixture may contain one or more other diols and/or divinyl ethers. Preferably, the mole ratio of diol(s) to divinyl ether(s) in the mixture is approximately 1:1, although the exact ratio may be varied to adjust the molecular weight of the resulting polymer. Higher molecular weights are generally achieved when the ratio is closer to 1:1. Lower molecular weights may be achieved by using a slight excess of either the diol(s) or the divinyl ethers, and/or by including small amounts of monofunctional alcohols and/or vinyl ethers. Preferably, the molecular weights of the resulting polyacetal (e.g., a polymer or copolymer comprising a recurring unit represented by the formulae (1) and/or (2)) are about 1,000 Daltons or greater, more preferably in the range of about 1,000 to about 250,000 Daltons.

Recurring units represented by the formula (I) encompass two genera, one in which X is selected from the group consisting of $C(O)OR^1$, $C(O)SR^1$, and $C(O)NR^1R^2$, and the other in which X is VZ. Polyacetals in which X is selected from the group consisting of $C(O)OR^1$, $C(O)SR^1$, and $C(O)NR^1R^2$ are useful for making polyacetals in which X is VZ. For example, polyacetals comprising a recurring unit of the formula (I) in which X is VZ and V is —C(O)NH— are preferably made by reacting a compound represented by the formula $H_2NZ$ with a polyacetal comprising a recurring unit of the formula (I) in which X is $C(O)OR^1$, as shown in formula (V):

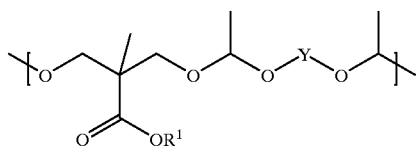

(V)

In formula (V), $R^1$ and Y have the same meanings as set forth above. For the compound represented by the formula $H_2NZ$, Z has the same meaning as set forth above. The reaction of the compound represented by the formula $H_2NZ$ with the polyacetal of the formula (V) is preferably conducted in a polar solvent such as dimethylformamide. The polyacetal of the formula (V) may be prepared by reacting a diol of the formula (III) in which X is —C(O)OR$^1$ with a divinyl ether of the formula (IV), under the general conditions described above for the polymerization of diols and divinyl ethers. A "polyacetal of the formula (V)" or "polymer of the formula (V)", as those terms are used herein, includes copolymers comprising a recurring unit of the formula (V) as well as homopolymers consisting essentially of recurring units of the formula (V).

It has been found that polyacetals of the formula (I) in which X is VZ form complexes with polynucleotides such as DNA and RNA. Thus, another embodiment provides a complex comprising a polyacetal of the formula (I) and a polynucleotide, in which the X in the polyacetal of the formula (I) is VZ, where V and Z have the same meanings as set forth above. Preferably, V is —C(O)NH—. Such complexes are preferably formed by intermixing the polyacetal of the formula (I) (in which X is VZ) and a polynucleotide. Preferably, such intermixing is conducted by adding a solution containing the polyacetal to a second solution containing the polynucleotide. Complexation may be verified by examining the retardation of the polynucleotide-polyacetal band on agarose gel electrophoresis, as shown in FIG. 1.

Figure 2:
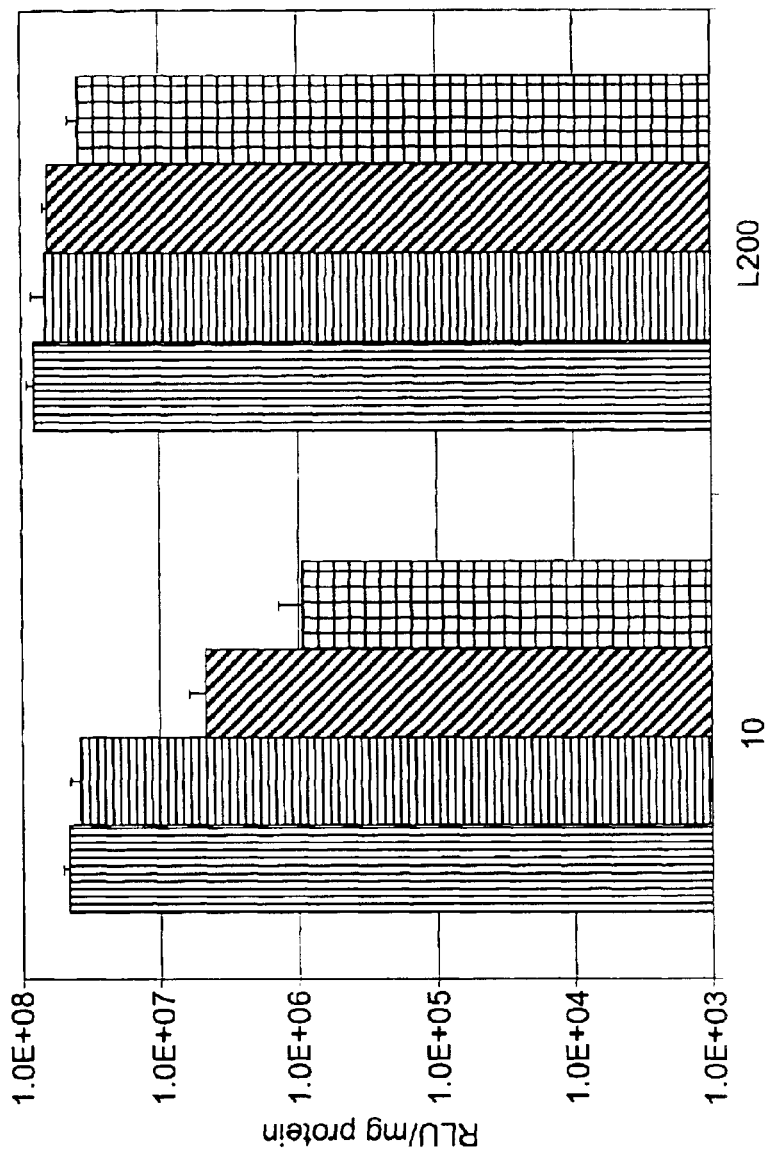
FIG. 2 shows a bar graph plotting Relative Light Units (RLU) per milligram of protein for transfection of human kidney embryonic cells ("293 cells") with plasmid DNA using polyacetal 10 and a commercial transfection reagent L2000 (Lipofectamine 2000, positive control). The results show that the transfection efficiency of polyacetal 10 is comparable to the best commercially available transfection agent currently known, Lipofectamine 2000.
Figure 4A:
FIG. 4 shows reproductions of photographs of GFP signals for 293 cells resulting from acidic degradation studies in pH 5.0 and pH 6.0 buffers after 24 hours and 48 hours. The results show that polyacetal 10 was substantially completely hydrolyzed at pH 5.0 or 6.0 within 24 hours.
Figure 4B:
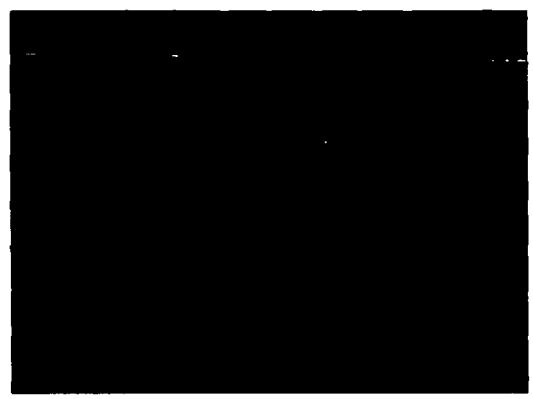
Figure 4C:
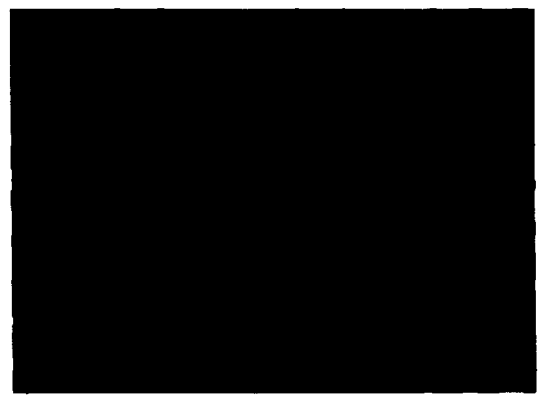
Figure 4D:

It has been found that complexes comprising polyacetals of the formula (I) (in which X is VZ) and polynucleotides are useful for transfecting cells. Transfection is preferably conducted by contacting the cell with the complex. The examples below illustrate the use of polyacetal-DNA complexes for the transfection of human embryonic kidney cells ("293 cells"), as shown in FIG. 2. It has been found that preferred complexes comprising polymers of the formula (I) (in which X is VZ) and polynucleotides are relatively non-toxic. The examples below illustrate the cytotoxicity of polyacetal-DNA complexes on mammalian cells as evaluated using a 3-[4,5 dimethylthiazol-2-yl]-2,5-diphenyltetrazolium bromide (MTT) method (see FIG. 6).

EXAMPLES

Cell lines and cultures used in the following examples were prepared as follows: Human embryonic kidney cells ("293 cells") grown in Dulbecco's-modified Eagle's medium (DMEM) containing 10% (v/v) heat-inactivated fetal bovine serum (FBS), 100U/ml Penicillin and 100 μg/ml streptomycin, and incubated at 37° C. at 100% humidity atmosphere containing 7.5% $CO_2$.

GFP plasmids used in the following examples were prepared as follows: Plasmid pCMV-GFP was purchased from Clonetech. The expression of green fluorescent protein (GFP) cDNA is controlled by human cytomegalovirus (CMV) promoter and the transcripts are stabilized by a gene expression enhancer, chicken β-globulin intron. The plasmid vector pCMV-luc was constructed by cloning the firefly luciferase gene into pCMV-0, with the same backbone of mammalian expression vector. The plasmid was expanded in DH5α E. coli and purified with Qiagen Plasmid Max Preparation Kit according to the manufacture's instructions. The quantity and quality of the purified plasmid DNA was assessed by spectrophotometric analysis at 260 and 280 nm as well as by electrophoresis in 0.8% agarose gel. Purified plasmid DNA was resuspended in sterile distilled, deionized $H_2O$ and frozen. The purified plasmid DNA may be referred to as "GFP plasmid" below. Green fluorescent signals in cells were observed under a fluorescent microscope (Olympus, filter 520 nm). Cells were photographed using a 10× objective. The percent of cells with GFP signal in transfected cultures was determined from counts of three fields.

Divinyl ether 4 was prepared from adipic hydrochloride and aminopropyl ether. Diol 5 was prepared by esterification of the corresponding carboxylic acid. All of the chemicals and reagents for the syntheses of polyacetals were purchased from Aldrich Chemical Co.

Examples 1–4

Figure 7:
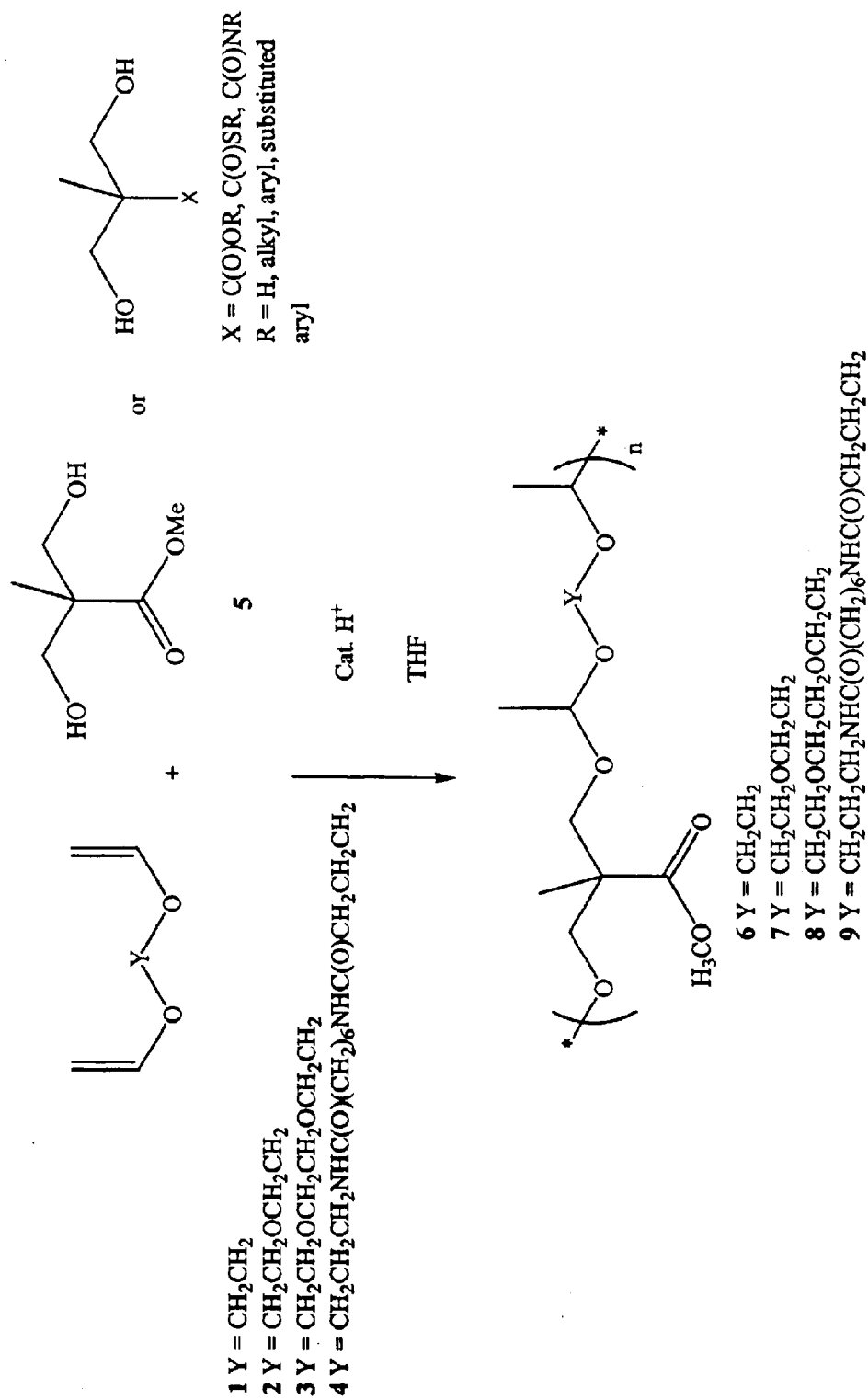
FIG. 7 shows a preferred reaction scheme for the synthesis of polyacetals 6–9.

Polyacetals 6–9 were prepared according to the reaction scheme shown in FIG. 7. The following description for the synthesis of polyacetal 7 is illustrative: Di(ethylene glycol) divinyl ether 2 (1.39 g, 8.76 mmol) and bis-(2-hydroxymethyl)methyl propionate 5 (1.30 g, 8.76 mmol) were mixed in tetrahydrofuran (THF) (10 mL) with molecular sieves (1.0 g) at room temperature and stirred for 20 min. A catalytic amount of toluensulfonic acid monohydrate (TSA, 0.015 g, 0.08 mmol) was added and stirring was continued for four days. The reaction mixture was quenched with sodium bicarbonate (1 mL, 5% in water) or triethylamine (1 mL). Water (10 mL) was added and the organic phase was extracted with ethylacetate (3×10 mL). The extracts were combined, dried with sodium sulfate, filtered, and concentrated by rotary evaporation. The residue was dried under high vacuum to give polyacetal 7 (2.65 g, 8.65 mmol, 98%) as an oil.

Examples 5–11

Figure 8:
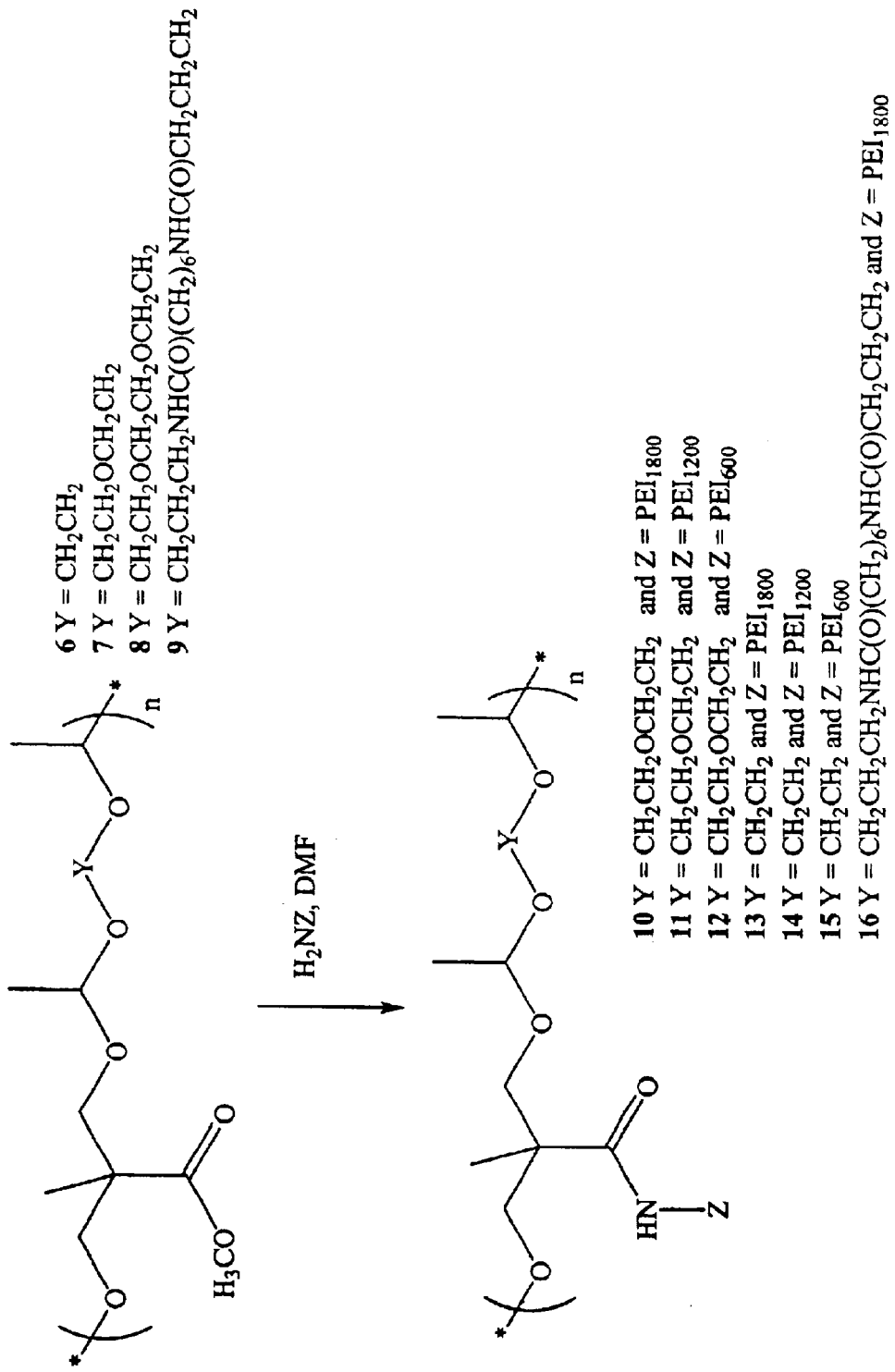
FIG. 8 shows a preferred reaction scheme for the synthesis of polyacetals 10–16.

Polyacetals 10–16 were prepared according to the reaction scheme shown in FIG. 8. The following description for the synthesis of polyacetal 10 is illustrative: To poly (ethylenimine) ($PEI_{1800}$) (30 g, 16.7 mmol) was added a solution of polyacetal 7 (0.5 g, 1.63 mmol) in dimethylformamide (DMF) (10 mL). Additional DMF (10 mL) was added and the mixture was stirred for four days. THF (100 mL) was added to form a precipitate. The precipitate was filtered and washed with THF, then dried under high vacuum to give polyacetal 10 (2.2 g).

Example 12

A polyacetal-poly(ethylenimine) conjugated with an enhancer was prepared as follows:

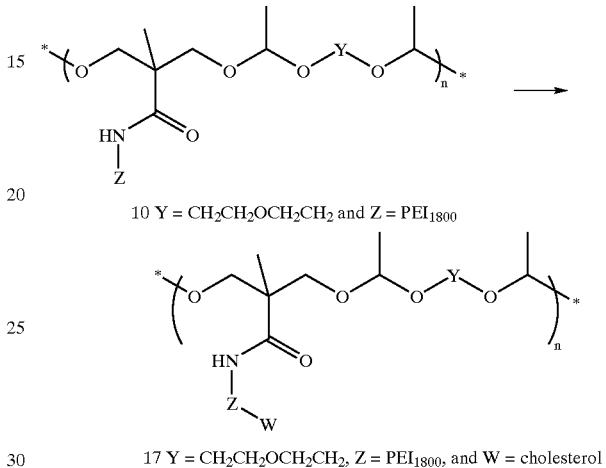

10 Y = $CH_2CH_2OCH_2CH_2$ and Z = $PEI_{1800}$

17 Y = $CH_2CH_2OCH_2CH_2$, Z = $PEI_{1800}$, and W = cholesterol

Figures 5A, 5B:
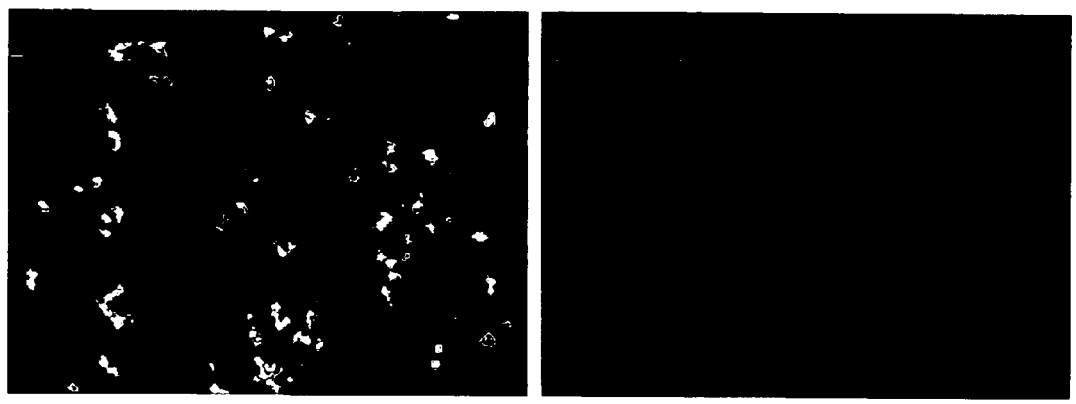
FIG. 5 shows reproductions of photographs of GFP signals for 293 cells using polyacetal 17 and poly(ethylenimine)-1800 (negative control). The results show that polyacetal 17 has a higher transfection efficiency than poly(ethylenimine)-1800.

Polyacetal 10 (0.55 g) and dimethylsulfoxide (DMSO) (50 mL) were combined in a vial. Cholesteryl chloroformate (1.0 g) and triethylamine (1 mL) were added and the resulting mixture was stirred for 20 minutes, filtered to remove an insoluble residue, and washed with dichloromethane (30 mL). The resulting solid residue was dried under high vacuum to give 1.3 grams of polyacetal 17. Polyacetal 17 was found to be more efficient as a transfection reagent in 293 cells than a poly(ethylenimine) control, as shown by GFP assay (FIG. 5).

Examples 13–24

A series of 12 polyacetal 10 samples were degraded in solutions (pH 7.4, pH 6.0, and pH 5.0) for 3 hours, 6 hours, 12 hours, and 24 hours at room temperature. These solutions were used for the transfection of 293 cells for the GFP assays discussed herein. FIG. 3 shows that the polyacetals were very stable at pH 7.4 (e.g., physiological blood pH). FIG. 4 shows that the polyacetals were substantially completely hydrolyzed at pH 5.0 or 6.0 (e.g, pH of endosome-lysosomes inside cells) within 24 hours.

Example 25

Retardation of polynucleotide-polyacetal complexes: Various amounts of polyacetals 10 and 12 in 10 μl DMEM (without serum and antibiotic) were added dropwise into 0.2 μg GFP plasmid in 10 μl DMEM (without serum and antibiotic) with vortexing. The resulting complexes were placed at room temperature for 15 min prior to electrophoresis. Five μl of loading dye was added to each sample, and 15 μl of each sample were loaded per well. The complexes were analyzed by electrophoresis in a 0.3% agarose gel with 0.04 M Tris-acetate buffer, pH 7.4, containing 1 mM EDTA, at 100V for 30 minutes. The complexes were visualized by UV illumination. The polynucleotide (plasmid DNA) complexed to the polyacetal was retarded in the agarose gel, so that greater retardation indicated greater binding between the polyacetal and the polynucleotide, as shown in FIG. 1.

Example 26

In vitro transfection using polyacetals 10 and 17 was carried out as follows: Permanent 293 cells were plated in 24-well tissue culture plates ($2 \times 10^5$ cells/well) and incubated overnight in DMEM with 10% fetal bovine serum (FBS). For each well, a 30 μl aliquot of polyacetal solution (each containing a different dose of polyacetal) was added dropwise into a 30-μl DNA solution containing 0.6 μg of plasmid DNA, e.g. pCMV-GFP plasmid DNA or pCMV-luc, while vortexing. Dropwise addition while vortexing was found to be highly preferable, because it was found that transfection results depended on the mixing conditions. The mixed DNA and polyacetal solutions were incubated for 15 minutes at room temperature to form DNA-polyacetal complexes. Then, 60 uL of DNA-polyacetal complex was added into each well and the cells were incubated (37° C., 7.5% $CO_2$) for 24 hours. After that incubation, GFP signals and fruitfly luciferase activities were detected as described below. Commercial transfection agent Lipofectamine 2000 (L2000) was used as a positive control according to the protocol provided by manufacturer.

Example 27

Luciferase activity was measured using a chemiluminescent assay following the manufacturer's instructions (Luciferase Assay System; Promega, Madison, Wis., USA). About twenty four hours after the transfections described in Example 26 above, the cells were rinsed twice with PBS and then were lysed with lysis buffer (1% Triton X-100, 100 mM $K_3PO_4$, 2 mM dithiothreitol, 10% glycerol, and 2 mM EDTA pH 7.8) for 15 min at room temperature. A 10-μl aliquot of cell lysate was then mixed with 50-μl of luciferase assay reagent with injector at room temperature in the luminometer. Light emission was measured in triplicate over 10 seconds and expressed as RLUs (relative light units). Relative light units (RLU) were normalized to the protein content of each sample, determined by BSA protein assay (Pierce, Rockford, Ill.). All the experiments were conducted in triplicate. The results obtained for the transfection of 293 cells with pCMV-luc using polyacetal 10 and L2000 (positive control) are shown in FIG. 2. These results show that the transfection efficiencies of these polyacetals are comparable to those achieved with the best commercially available transfection agent (Lipofectamine 2000) currently known.

Example 28

Figure 6:
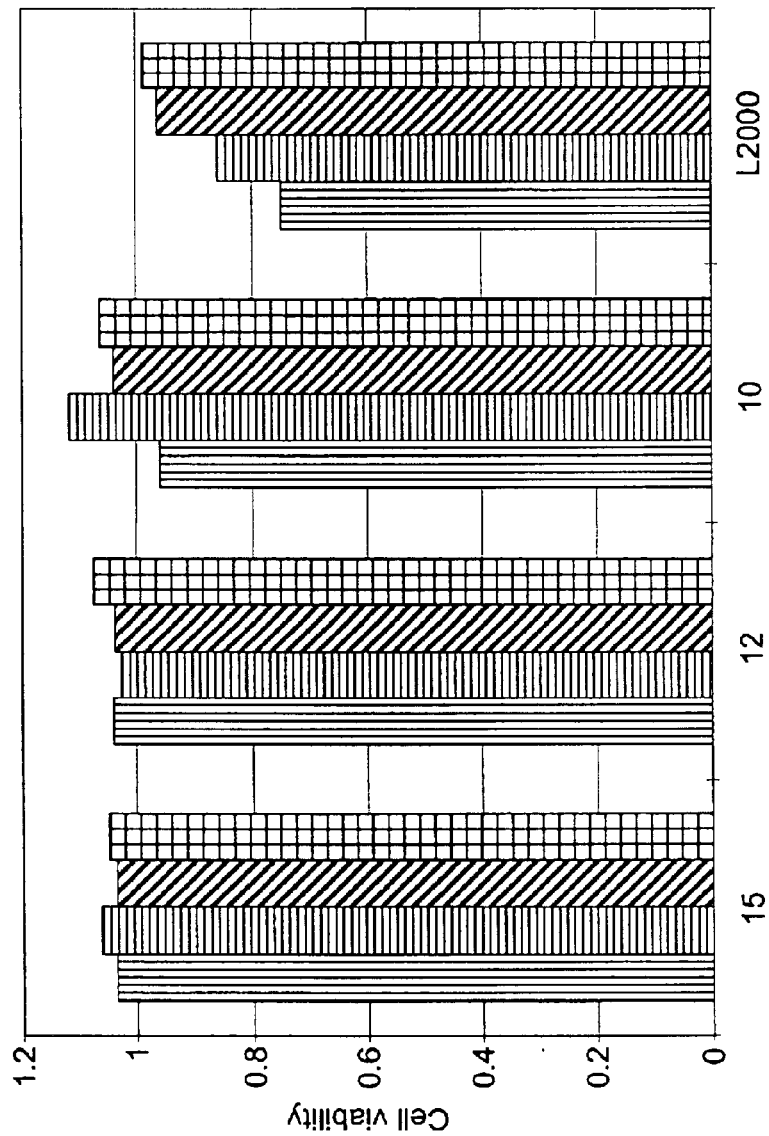
FIG. 6 shows a bar graph plotting Cell Viability (%) of 293 cells. Polyacetals 15, 12, and 10 do not display cytotoxicity in this assay.

The cytotoxicities of polyacetals 10, 12 and 15 on mammalian cells were evaluated using the 3-[4,5-dimethylthiazol-2-yl]-2,5-diphenyltetrazolium bromide (MTT) method. In this method, 96-well plates were seeded with 293 cells ($4 \times 10^4$ cells/well) and the cells incubated for 24 hours. Various amounts of polyacetal-DNA complexes prepared as described in Example 26 were added to the cells for a period of 3 hours. The media was then removed and fresh media added. Following further incubation for 48 hrs, the media was removed and 10 μl of MTT solution (5.0 mg/ml) was added to each well, and incubated for 3 hrs. The medium was then removed and 200-μl DMSO was added to dissolve the formazan crystals. The absorbance of the solution was measured at 570 nm. Cell viabilities was calculated using the equation: Viability (%)={$Abs_{570\ (sample)}$/$Abs_{570\ (control)}$}×100. All the experiments were conducted in triplicate. The results shown in FIG. 6 show that the polyacetals were less toxic to cells than Lipofectamine.

What is claimed is:

1. A polymer comprising recurring units represented by formula (I):

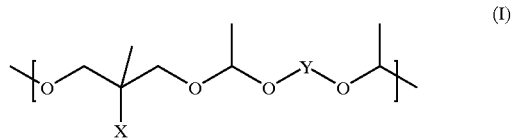

(I)

wherein X is selected from the group consisting of $C(O)OR^1$, $C(O)SR^1$, $C(O)NR^1R^2$, and VZ, where $R^1$ and $R^2$ are each individually selected from the group consisting of hydrogen, $C_1$ to $C_{10}$ alkyl, and $C_6$ to $C_{10}$ aryl, where V is a labile linker group, and where Z is selected from the group consisting of poly (ethyleneimine), poly(propyleneimine), poly(lysine), PAMAM dendrimer, octaamine dendrimer, and hexadecaamine dendrimer; and wherein Y is selected from the group consisting of —($CH_2$)$_2$—, —($CH_2$)$_2$—O——($CH_2$)$_2$—, —($CH_2$)$_2$—O—($CH_2$)$_2$—O—($CH_2$)$_2$—, and —($CH_2$)$_3$—NHC(O)—($CH_2$)$_6$—C(O)NH—($CH_2$)$_3$—.

2. The polymer of claim 1 in which Z is poly (ethyleneimine).

3. The polymer of claim 2 in which the poly (ethyleneimine) has a molecular weight in the range of about 200 to about 100,000 Daltons.

4. The polymer of claim 1 in which Z is poly(lysine).

5. The polymer of claim 4 in which the poly(lysine) has a molecular weight in the range of about 200 to about 50,000 Daltons.

6. The polymer of claim 1 in which X is VZ.

7. The polymer of claim 6 in which V is —C(O)NH—.

8. The polymer of claim 1, further comprising a recurring unit represented by the formula (II):

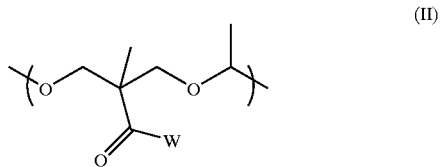

(II)

wherein W is selected from the group consisting of an enhancer and a targeting receptor.

9. The polymer of claim 8 in which W is an enhancer and a targeting receptor.

10. The polymer of claim 8 in which W is selected from the group consisting of lipid, cholesterol, transferrin, antibody, antibody fragment, galactose, mannose, lipoprotein, lysosomotrophic agent, and fusogenic agent.

11. The polymer of claim 8 in which X is VZ and in which Z is conjugated to W or to a substance selected from the group consisting of a second enhancer and a second targeting receptor.

12. A method of making the polymer of claim 1, comprising reacting a diol represented by the formula (III) with a divinyl ether represented by the formula (IV):

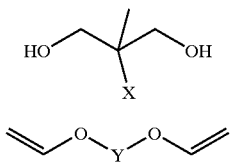
(III)

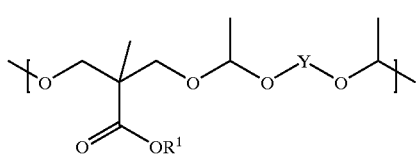
(IV)

wherein X and Y have the same meanings as set forth in claim 1.

13. A method of making the polymer of claim 7, comprising reacting a compound represented by the formula H$_2$NZ with a polymer comprising a recurring unit of the formula (V):

(V)

wherein Z is selected from the group consisting of poly(ethyleneimine), poly(propyleneimine), poly(lysine), PAMAM dendrimer, octaamine dendrimer, and hexadecaamine dendrimer; and wherein Y is selected from the group consisting of —(CH$_2$)$_2$—, —(CH$_2$)$_2$—O—(CH$_2$)$_2$—, —(CH$_2$)$_2$—O—(CH$_2$)$_2$—O—(CH$_2$)$_2$—, and —(CH$_2$)$_3$—NHC(O)—(CH$_2$)$_6$—C(O)NH—(CH$_2$)$_3$—.

14. A complex comprising the polymer of claim 6 and a polynucleotide.

15. A method for making the complex of claim 14, comprising intermixing the polymer of claim 6 and the polynucleotide.

16. The method of claim 15 in which the intermixing is conducted by adding a solution comprising the polymer of claim 6 to a second solution comprising the polynucleotide.

17. The method of claim 16 in which the V in the polymer of claim 6 is —C(O)NH—.

18. A method for transfecting a cell, comprising contacting the cell with the complex of claim 14.

19. The method of claim 18 in which the V in the polymer of claim 6 is —C(O)NH—.

20. The method of claim 19 in which the Z in the polymer of claim 6 is poly(ethyleneimine).

* * * * *